United States Patent [19]
DiFoggio et al.

[11] Patent Number: 5,668,374
[45] Date of Patent: Sep. 16, 1997

[54] METHOD FOR STABILIZING NEAR-INFRARED MODELS AND DETERMINING THEIR APPLICABILITY

[75] Inventors: Rocco DiFoggio, Houston, Tex.; Martha L. Ranc, Robbinsville, N.J.

[73] Assignee: Core Laboratories N.V., Amsterdam, Netherlands

[21] Appl. No.: 646,082

[22] Filed: May 7, 1996

[51] Int. Cl.⁶ ................... G01J 3/28; G01J 3/42
[52] U.S. Cl. ............... 250/339.12; 250/339.09; 364/498
[58] Field of Search ............ 250/339.07, 339.09, 250/339.12, 343; 364/498, 502

[56] References Cited

U.S. PATENT DOCUMENTS

| | | | |
|---|---|---|---|
| 4,800,279 | 1/1989 | Hieftje et al. | 250/339.09 |
| 4,944,589 | 7/1990 | Nordqvist | 356/326 |
| 5,291,426 | 3/1994 | Collins et al. | 364/574 |
| 5,303,165 | 4/1994 | Ganz et al. | 364/571.01 |
| 5,308,982 | 5/1994 | Ivaldi et al. | 250/339.01 |
| 5,317,378 | 5/1994 | Mould et al. | 356/301 |
| 5,360,972 | 11/1994 | DiFoggio et al. | 250/339.12 |
| 5,397,899 | 3/1995 | DiFoggio et al. | 250/339.09 |
| 5,428,558 | 6/1995 | Cahill et al. | 364/571.02 |
| 5,428,696 | 6/1995 | Cahill et al. | 385/16 |
| 5,504,332 | 4/1996 | Richmond et al. | 250/339.12 |

OTHER PUBLICATIONS

DiFoggio, Rocco, "Examination of Some Misconceptions About Near-Infrared Analysis", Applied Spectroscopy, vol. 49, No. 1, Jan. 1995, pp. 67–75.

DiFoggio, R., Sadhukhan, M. & Ranc, M. L., "Near-Infrared Offers Benefits And Challenges in Gasoline Analysis", Oil & Gas Journal May 3, 1993, pp. 87–90.

Naes, T. & Isaksson, T., "The Importance of Outlier Detection in NIR Spectroscopy", NIR News, vol. 3, No. 4, 1992, pp. 12–13.

Shenk, J.S., & Westerhaus, M.O., "Population Definition, Sample Selection, & Calibration Procedures For Near-Infrared Spectroscopy", Crop Science, vol. 31, No. 2, Mar.–Apr. 1991, pp. 469–474.

*Primary Examiner*—David P. Porta
*Assistant Examiner*—David Vernon Bruce
*Attorney, Agent, or Firm*—Madan & Morris, PLLC

[57] ABSTRACT

This invention provides a method for infrared and near-infrared estimations of properties of materials with improved model stability against random and pseudo-random effects and improved assessment of the appropriateness of the model for an unknown sample. Statistical tests are defined for quantifying the model's stability against random effects (B-statistic) and the probability of substantial interpolation error (I-statistic). The method of this invention involves building many different infrared models for each property of interest, either randomly or by other strategies. The models with the lowest calibration errors for their respective calibration sets whose errors are least correlated to one another are averaged to create a composite model. Such composite models have improved stability and accuracy. The consistency with which the individual models (making up the composite model) estimate the same property value for an unknown sample is a measure of the improbability of substantial interpolation error.

23 Claims, 5 Drawing Sheets

ABSORBANCE AT A WAVELENGTH

OUTLIER
$D_i > \sqrt{3 \langle D^2 \rangle}$

ABSORBANCE AT ANOTHER WAVELENGTH

FIG. 4

ABSORBANCE AT A WAVELENGTH

INLIER
NEAREST NEIGHBOR $> \sqrt{0.6 \langle D^2 \rangle}$ AWAY
AND/OR RESPONSE SURFACE "HILLY"

ABSORBANCE AT ANOTHER WAVELENGTH

METHOD FOR STABILIZING NEAR-INFRARED MODELS AND DETERMINING THEIR APPLICABILITY

BACKGROUND OF THE INVENTION

1. Field of Invention

This invention relates generally to a method for estimation of properties of materials by near-infrared analysis through improved spectral-model stability and accuracy and through improved ability to ascertain the applicability of a spectral model to an unknown. A particular example of this method is improved estimation of the octane numbers of gasolines by near-infrared (NIR) analysis.

2. Description of the Related Art

Because materials of different chemical compositions exhibit measurable differences in their absorption of infrared radiation, near-infrared (NIR) analysis or mid-infrared analysis can be used to estimate both the chemical composition of material and the physical properties of materials which result from their chemical composition.

NIR analysis is currently a common method for analyzing agricultural products. For example, NIR is used to analyze the protein content of wheat and other grains. In recent years, NIR also has been applied in the petrochemical industry for analysis of both chemical composition (e.g. aromatic and saturates content) and physical properties (e.g. octane number, density, vapor pressure) of hydrocarbons including gasoline.

NIR analysis has been of particular interest in the field of octane measurement for gasoline. Octane number ratings are a measure of the resistance of a gasoline to engine knock. There are two basis types of octane number ratings corresponding to two different sets of conditions under which the engine test is performed. For the same gasoline, the less severe test (Research Octane Number or RON) results in a higher octane number rating than does the more severe test (Motor Octane Number or MON). The average of RON and MON is often called Pump Octane Number (PON) because it is the number which is posted on gasoline station pumps. Pump Octane Number is alternatively called Road Octane Number because it represents the average performance of a gasoline under conditions of varying severity as one would likely encounter when actually driving down a road.

Historically, octane has been directly measured in test engines, where one listens for a knock in the engine, where the knock is the uncontrolled explosion of the last portion of the fuel-air mixture in the cylinder. An empirical scale was determined in the 1930's for octane wherein pure iso-octane was defined as 100, normal heptane as 0 and mixtures of the two were used to define intermediate octane numbers. Large one-cylinder engines are used for the direct measurement of the octane rating of a gasoline by comparing the intensity of the knock of the gasoline to that of a standard mixture of iso-octane and normal heptane and adjusting the compression ratio until the knock intensity of the gasoline is the same as for the standard prior to the adjustment.

Octane measurement using a knock engine is considered the primary analytical technique for determining the octane rating of a gasoline. NIR analysis on the other hand is a secondary analytical technique that is calibrated against the primary analytical technique. Typically, the primary analytical technique for any type of measurement is somewhat slow and cumbersome. As a secondary technique, NIR analysis is a fast and convenient method of inferring the chemical and physical properties of a substance. Regardless of the material to be analyzed, NIR analysis requires a training set of samples of the material for which one obtains both the near-infrared spectra and the primary lab measurements of the properties of interest.

Using regression mathematics, one then correlates the NIR spectra of the calibration set to the primary reference method measurements of the properties of these samples. The resulting regression equations allow one to estimate the properties of unknown samples of material (ones for which primary lab measurements have not been made) directly from their NIR spectra.

Chemometric techniques are often used to relate one set of properties of a sample (which is difficult or time-consuming to measure directly) to another set of properties (which is easier and faster to measure directly). For example, within seconds, one can estimate the protein content of wheat from the near-infrared reflection spectra of the flour. Similarly, a complicated physical property such a octane number can be related to the near-infrared transmission spectra of the gasolines.

Infrared spectra contain information about the number and type of functional groups that are associated with a sample's chemical composition. Infrared spectra are simply measurements of absorbance (sample darkness) versus wavelength or wavenumber (infrared "color"). Absorbance (rather than percent transmittance) is used for quantitative spectroscopy because, according to Beer's law, it is the absorbance which is proportional to the concentration of the absorbing species.

For transmission spectroscopy (light going completely through the sample), the absorbance, A, at a wavelength, $\lambda$, is defined as the base-ten logarithm of the ratio of intensity of light, $I_{\lambda o}$, at wavelength $\lambda$, which enters the sample to the intensity of light $I_\lambda$, at wavelength $\lambda$, which exits the sample as shown in Equation 1:

$$A_\lambda = \log_{10}(I_{\lambda o}/I_\lambda) \qquad (1)$$

Therefore, 100% transmittance corresponds to zero absorbance, 10% transmittance corresponds to one unit of absorbance and 1% transmittance corresponds to two absorbance units. Notice that there is a nonlinear logarithmic relationship between transmittance, $T_\lambda = I_\lambda/I_{\lambda o}$ and the absorbance, $$A_\lambda = \log_{10}(1/T_\lambda).$$

To perform near-infrared calibration, one first obtains the near-infrared spectra of a training set of samples for which the properties of interest have been measured by traditional analytical techniques. Next, one tries to develop a regression equation (model) that relates the training set spectra to the properties. It is possible to correlate NIR spectra to physical properties such as octane number because these physical properties ultimately depend on chemical composition—albeit in complex, and often unknown, ways.

Equation 2 shows the final form of linear models regardless of whether they were obtained by multiple linear regression, principal components regression, or partial least squares regression. The model consists of those constants $C_0, C_1, C_2 \ldots C_N$ that provide the best fit between the property of interest and the training set spectra. Here, $A_1, A_2, \ldots A_N$ are the absorbances at wavelengths $\lambda_1, \lambda_2, \ldots \lambda_N$ which, taken collectively, constitute the spectrum.

$$\text{Property} = C_0 + C_1 A_1 + C_2 A_2 + \ldots + C_N A_N \qquad (2)$$

Any model which is designed to fit a particular set of points is at risk for interpolation (inlier) errors and/or extrapolation (outlier) errors in those regions where there are no data points. This can easily be illustrated with a simple one-dimensional example.

Consider the function F(x) given in Equation 3. It consists of a linear function of x, plus a quadratic function of x (that rapidly fades away when x<2), plus a cubic function of x (that rapidly fades away with distance from x=1).

$$F(x)=x+(x-2)^2[\tanh(5(x-2))]+(x-1)^3[300e^{-20(x-1)(x-1)}] \quad (3)$$

Figure 1:
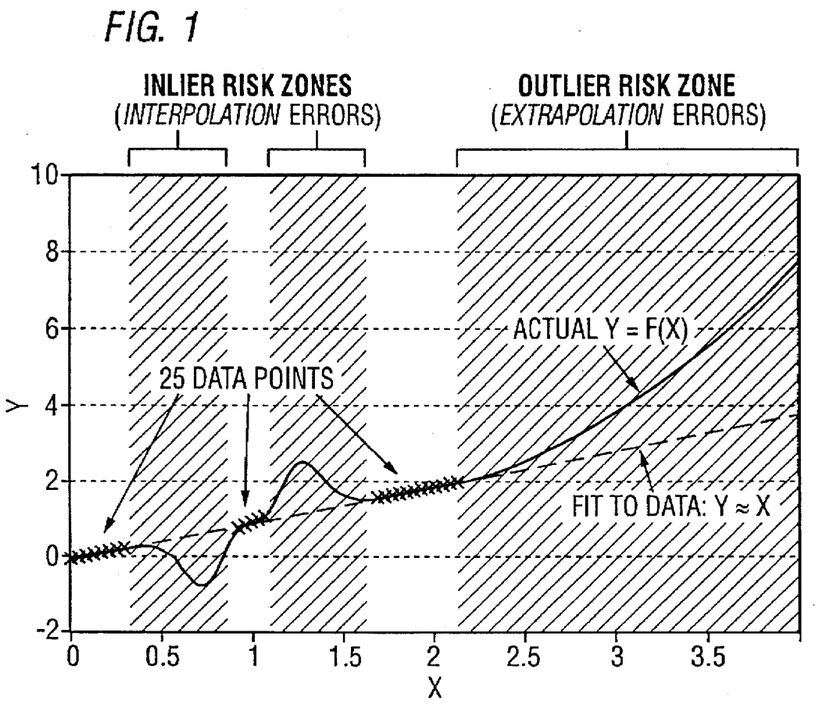
FIG. 1 illustrates that inliers and outliers can occur where there are no data points.

The solid curve in FIG. 1 is a plot of F(x) from x=0 to x=4. Table 1 lists 25 values of F(x) that were calculated from Equation 1 for selected values of x. These (x,y) data points are displayed as X's in FIG. 1. Notice that the values of x were carefully chosen so as to skip the valley and hill around x=1 and to stop before x=2 where the quadratic component of F(x) begins to dominate over the linear component.

For the data points listed in Table 1, one can build a simple linear model, Y≈X, as shown by the dashed line in FIG. 1. The best linear fit to these data is the line Y=1.004X−0.002 which has an excellent correlation coefficient (R=0.999) and a superbly low standard error of calibration (0.027). Despite these seemingly good statistics, the model fails conspicuously around x=0.7, around x=1.3, and beyond x=2.

The point of this example is that no matter how good the correlation coefficient nor how low the standard error of calibration (SEC), a model is at risk for significant error in any region where there are no data points. Those regions that lie beyond the bounds of the data used are referred to as outlier risk zones. They are the places where extrapolation errors may occur. Inlier risk zones, on the other hand, are the gaps within the bounds of the data used in the model. They are places where model interpolation errors may occur. A good test exists for outliers (the Mahalanobis distance from the centroid of the data), but not for inliers.

To extend the discussion of inliers and outliers to functions of more than one variable, it is useful to define the Mahalanobis distance. The Mahalanobis distance, D, is a generalization of the familiar Euclidean distance, d, in which the measurement of distance is distorted along the principal directions of variation of the training set spectra.

Euclidean distance: $d^2=x'Ix=\Sigma x_i x_i = \Sigma x_i^2$ (4)

Mahalanobis distance: $D^2=x'(XX^t)^{-1}x=\Sigma x_i M_{ij} x_j$ (5)

where X=matrix of mean-centered calibration spectra
(or the scores of the principal components or the scores of the latent variables of these spectra)

$XX^t=N(XX^t/N)$=number of samples times covariance matrix $(XX^t)^{-1}$=inverse of number of samples times covariance matrix x=a spectrum whose distance from the center is sought or the difference between two spectra whose relative distance is sought.

One theorem associated with the Mahalanobis distance is that the root-mean-square (RMS) Mahalanobis distance is equal to the square root of the number of fitting parameters, k, used by the model divided by the number, N, of calibration samples that the model is fitting with these parameters. That is, $$D_{RMS}=(k/N)^{1/2} \quad (6)$$

Figure 2:
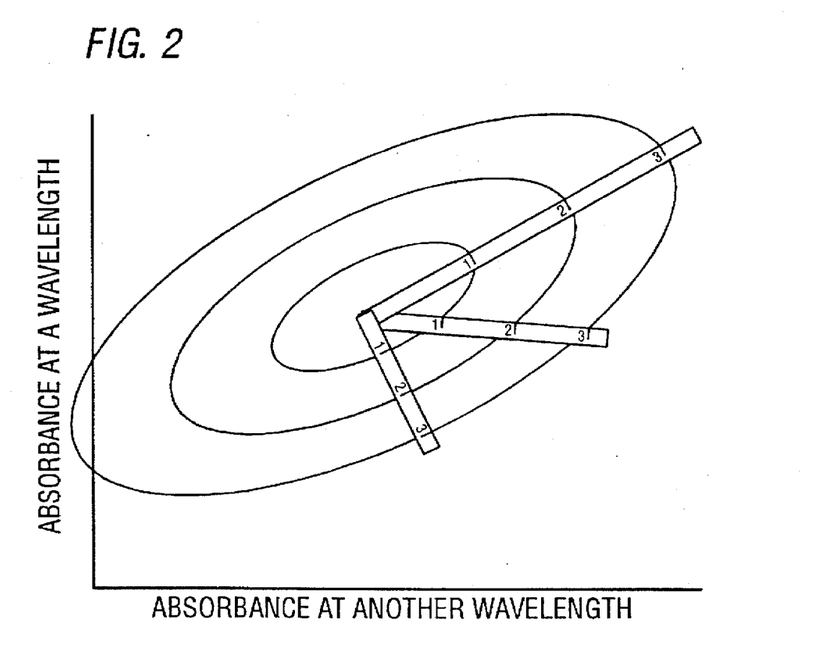
FIG. 2 illustrates that the scale of the Mahalanobis "ruler" varies with direction.

As shown in FIG. 2, one can think of the Mahalanobis distance (M-distance) as something which is measured by a special ruler that stretches and compresses with orientation. Often, the M-distance is expressed in units of root-mean-square M-distances. This "standardized" M-distance can be thought of as a generalization of the concept of standard deviation to multiple (and possibly correlated) dimensions. Samples are described as being 1, 2, or 3 M-distances away from the center of the cloud of spectral data points in much the same way as measurements might be described as being 1, 2, or 3 standard deviations away from the average of the measurements.

Figure 3:
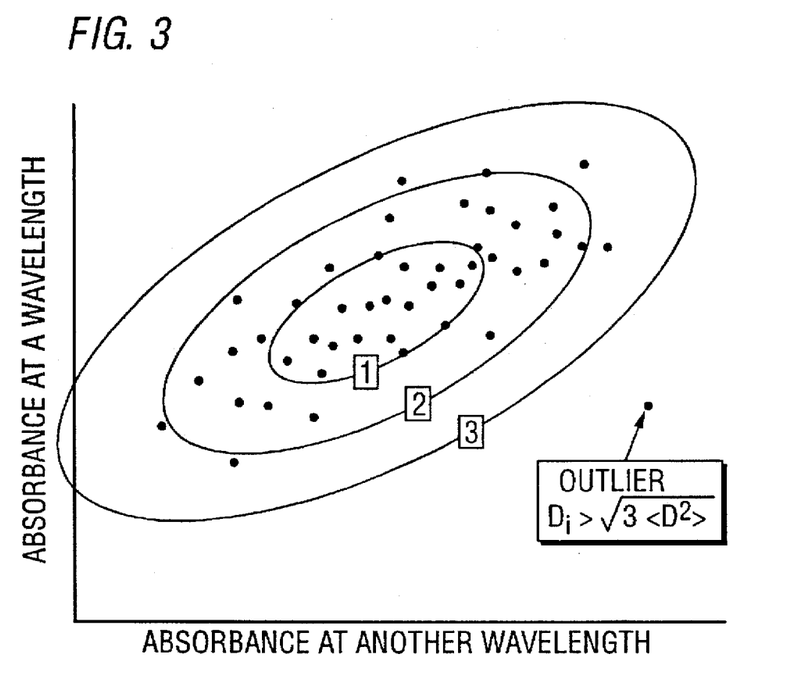
FIG. 3 illustrates an outlier spectrum using a Mahalanobis analysis.

As shown in FIG. 3, an outlier is a sample that lies outside the cloud of calibration set points. It is at risk for NIR model extrapolation error. The M-distance can be used to test for outliers. Typically, the outlier cutoff is taken to be somewhere between the square-root-of-2 and 2 times the root-mean-square Mahalanobis distance from the center of the cloud of data points.

Figure 4:
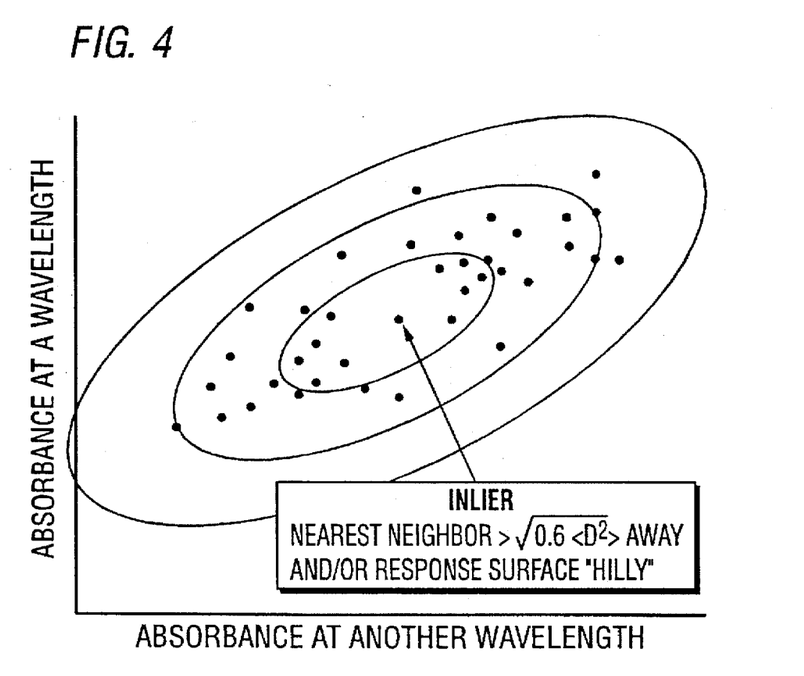
FIG. 4 illustrates an inlier spectrum using the Shenk and Westerhaus definition of an inlier.

As shown in FIG. 4, an inlier is a sample that resides in a gap in the cloud of calibration set samples. An inlier is at risk for NIR model interpolation error. As described in their article entitled "Population Definition, Sample Selection, and Calibration Procedures for Near-Infrared Reflectance Spectroscopy," Crop Science, 31, 469 (1991), J. S. Shenk and M. O. Westerhaus (Shenk and Westerhaus) used a "no-nearest-neighbor" cutoff of 0.6 Mahalanobis distance to define an inlier. One problem with the Shenk and Westerhaus definition is that it is too strict in regions where the response surface of the property of interest is flat and too lenient in regions where the response surface of the property of interest is "hilly."

It is analogous to a surveyor saying that he can generate accurate elevation maps if he has an elevation point every 10 miles. In flat deserts, 10 miles would be an unnecessarily frequent sampling rate, while in rugged, mountainous regions, 10 miles would be an inadequately sparse sampling rate because an entire hill or valley could be missed.

Figure 5:
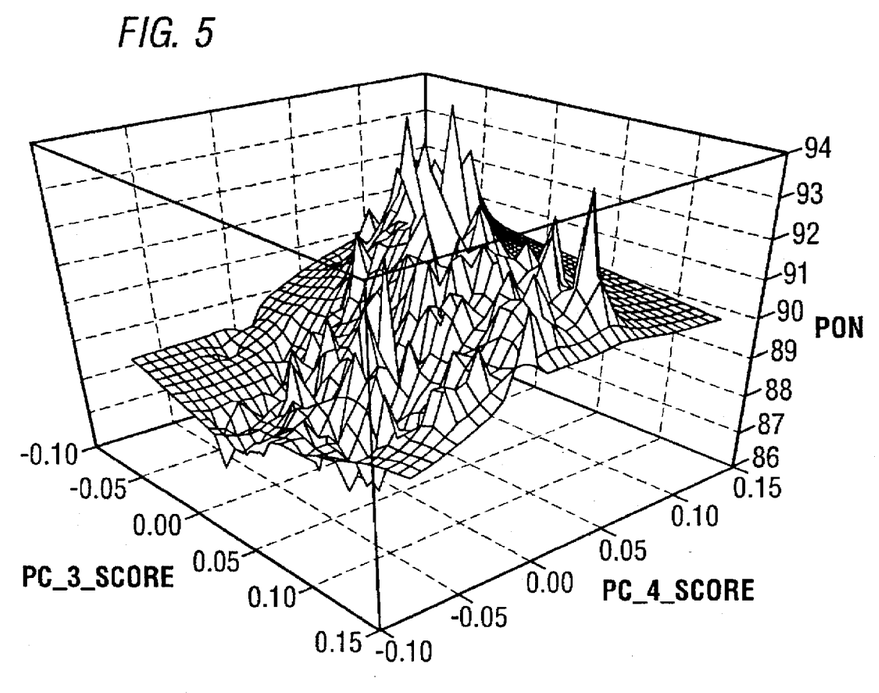
FIG. 5 illustrates a pump octane number response surface.

This issue is of considerable practical importance, especially when using NIR to estimate physical properties such as octane number that have very complicated response surfaces. FIG. 5 shows that the pump octane number response surface is very "hilly." Here it is seen plotted against those two principal component scores that, together, account for 81% of the variance of the pump octane number.

Thus, the Shenk and Westerhaus method for determining inliers in a set of data has several deficiencies. It is unable to automatically take into account how rapidly the local response surface is changing relative to the local spectral spacing of the calibration samples. It would be desirable to automatically "adjust" to the ruggedness of the response surface terrain. Other practical problems with using the Shenk and Westerhaus definition of an inlier are that it requires one to keep the calibration set handy at the application location and that it takes a very long time (despite using a computer) because one must compute the M-distance from an unknown to each and every calibration set sample. On information and belief, the Shenk and Westerhaus method for determining inliers is the only prior art test for inliers, and it is quite slow and, for many response surfaces, unreliable. Thus, it is desirable to have a fast and reliable test for inliers and a method to estimate the degree of risk for significant model interpolation error (the inlier probability) at any point in the inlier risk zones.

SUMMARY OF THE INVENTION

The present invention provides a method for determining a property of interest of a sample, which contains the steps of: (a) obtaining a plurality of samples of a material having known values of the property of interest; (b) determining a near-infrared spectrum of each of the samples in the plurality of samples; (c) grouping the samples in the plurality of samples into a plurality of subsets; (d) determining a regression model utilizing the near-infrared spectra of the samples for each of the subsets for estimating the value of the property of interest of the sample having unknown property of interest; (e) selecting regression models which have a standard error of calibration less than a predetermined value; (f) retaining regression models from the selected models whose residuals are relatively poorly correlated to each other; (g) averaging the retained models to determine a composite model; and (h) determining the property of interest of the unknown sample by utilizing the composite model.

The method may further be used to estimate the probability of significant interpolation error by the composite model (inlier detection) based on the disparity in the predictions of an unknown sample by the different individual models used in the composite model.

Examples of the more important features of the invention have been summarized rather broadly in order that the detailed description thereof that follows may be better understood, and in order that the contributions to the art may be appreciated. There are, of course, additional features of the invention that will be described hereinafter and which will form the subject of the claims appended hereto.

BRIEF DESCRIPTION OF THE DRAWINGS

For a detailed understanding of the present invention, references should be made to the following detailed description of the preferred embodiment, taken in conjunction with the accompanying drawings, in which like elements have been given like numerals and wherein.

DETAILED DESCRIPTION OF THE PREFERRED EMBODIMENTS

The present invention provides a method for improving infrared estimations of properties of materials by improving the infrared model's stability against random effects (such as spectral noise or the degree to which the particular samples used in one's calibration set are representative of other samples of the same material) and by improving the model's stability against pseudo-random effects (such as unforeseen chemical contaminants) and by improving one's ability to determine whether an unknown is an inlier for that model (that is, a sample which is at risk for substantial model interpolation error, and therefore, a sample for which the model may not be appropriate).

Using the present invention, one can quantify the qualitative concepts of stability against random effects and of appropriateness of a model for unknowns. That is, the robustness of a model against random effects can be quantified in terms of a "Ballast" or B-statistic. The likelihood that a sample (which has been shown not to be an outlier) is an inlier can be quantified in terms of an "Inlier" or I-statistic.

The method according to this invention involves building many different infrared models for each property (either randomly or by strategies to be described later). One discards all but the "best" models. That is, one discards all models except those that fit their respective calibrations sets to at least some desired Standard Error of Calibration (SEC). This SEC cutoff should be chosen to be close to the uncertainty in the lab values used for calibration without being less than it (which would imply overfitting). Next, one compares the remaining (best) models to one another in two ways.

First, one compares the residuals (the differences between the infrared estimations and the traditional lab values for each sample) of the different models for all those samples that the models have in common. This is done so that one can select those models whose residuals are the least correlated to one another because they are the models that would benefit the most from averaging when one is trying to create a very stable average model.

Secondly, one compares the variance (standard deviation squared) of the different infrared models' property estimations of each sample. Samples for which the standard deviation of the different models' estimations substantially exceeds the average standard error of calibration of these models are samples whose spectra lie in regions of spectral space that are too sparsely populated for the amount of response-surface curvature to be reliably interpolated by the model or samples whose spectra lie too far away from the centroid of the data to be reliably extrapolated. That is, such samples are likely to be inliers or outliers. If one has already used a standard test (such as the Mahalanobis distance from the centroid of the data) to eliminate the possibility that these samples are outliers, then these samples must be inliers.

The present invention defines an Inlier or I-statistic that tests the probability that an unknown is an inlier. Unlike prior art, the I-statistic of the present invention is a function of the spectrum that can be computed very quickly and does not require keeping the calibration set handy. The I-statistic is simply a formula into which one plugs an unknown spectrum and gets a number which is then compared to a standard F-distribution.

Figure 6:
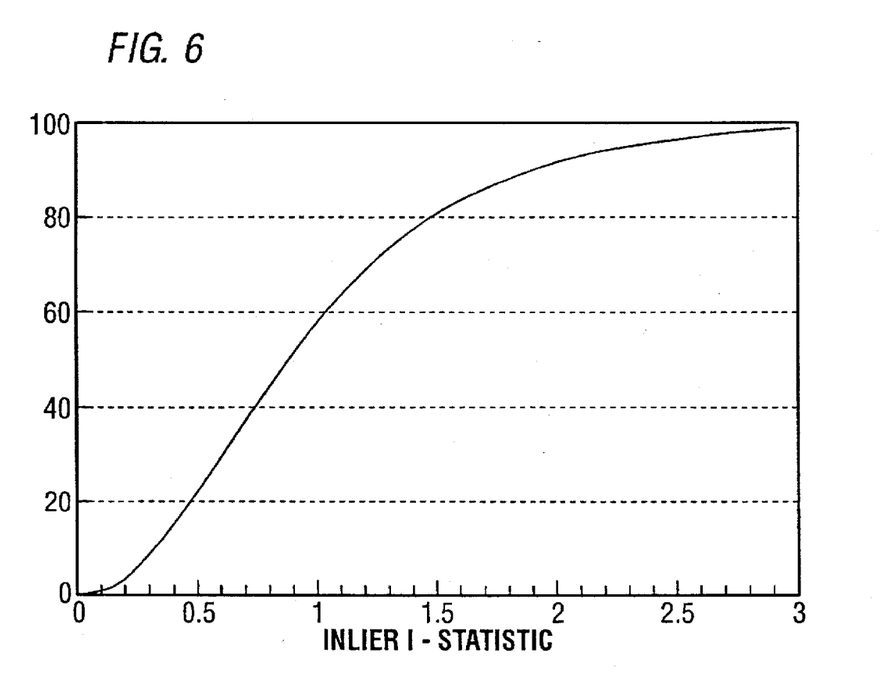
FIG. 6 provides an example of inlier probability versus the I-statistic.

FIG. 6 shows a typical I-statistic plot (corresponding to 5 degrees of freedom for the numerator and 650 degrees of freedom for the denominator). As usual, one sees that the transition from unlikely to likely inlier occurs near I=1. In this example, if the I-statistic for an unknown spectrum is computed to be 0.5, then there is about a 20% chance that the unknown is an inlier, whereas, if the I-statistic is 2.5, then there is about a 95% chance that the spectrum is an inlier.

The following hypothetical example illustrates how one may use near-infrared analysis, according to the present invention. Although analysis of gasoline, particularly octane number as the property of interest, is used as an example, the present invention is not limited to gasoline analysis. The present invention is equally applicable to the analysis of various other materials such as aviation fuels, diesel fuels, and refinery component streams, such as alkylate, reformate, raffinate, etc. The properties of interest may include, among other things, cetane number, flash point, cloud point and chemical properties such as percent of aromatics, etc.

Applying the present invention to gasoline analysis, for example, one may start with a training set of 100 spectra of gasoline samples with known Pump Octane Numbers (PON). The spectra are obtained by subjecting each gasoline sample to a known infrared light energy to excite vibrational, rotational, or electronic modes of the sample. The photons passing through the sample that are not involved in excitation are collected and converted into electrical signals. The electrical signals are then processed to provide a spectrum for each gasoline sample using known methods. Next, one builds a series of regression models on large subsets of this training set (e.g. on 80-sample subsets of the 100 spectra). One builds Model Number #1 based on randomly selected subset 1, Model #2 based on randomly selected subset 2, and so on, up to Model #30 based on randomly selected subset 30.

In this example, the subsets consist of the entire spectrum of some of the samples. Alternatively, the subsets may consist of different parts of the spectrum of all of the samples. Also, the subsets do not have to be selected randomly. Sometimes it is advantageous to use additional knowledge about the samples, such as whether they contain methyl tert-butyl ether (MTBE), to decide how one should divide the training set into the subsets that will be used to generate multiple models.

Next, one keeps only the best models for further examination. For example, the best models kept might be Models #2, #4, #6, #7, #9, #12, #17, #21, #26, and #28. The best PON models should have Standard Errors of Calibration (SEC) for PON that are less than about 0.35 octane numbers because this is close to, but not less than, the inherent imprecision in a knock engine measurement, which is the primary measurement.

An NIR model's residuals are the differences between the NIR-estimated values of a property and the directly-measured lab values. For each possible pair of models, one computes the correlation coefficient between the two models' residuals for those samples that were used in both models.

From this correlation table, one can select those models whose residuals are the least correlated to one another. Next, one averages these least correlated-models to create a composite or average model. For example, Average_Model= (#4+#6+#7+#12+#26)/5.0.

One estimates the degree of improvement of the composite (averaged) model predictions using a "ballast" or B-statistic which is defined as $(1-R^2)$, where R is the average correlation coefficient between residuals of the different models. A "high-ballast" model will generally have lower regression coefficients (for reduced amplification of noise and artifacts) and will be more resistant to spectral noise and to small amounts of unanticipated chemical interferents that occur in one region of the spectrum but not another.

Figure 7:
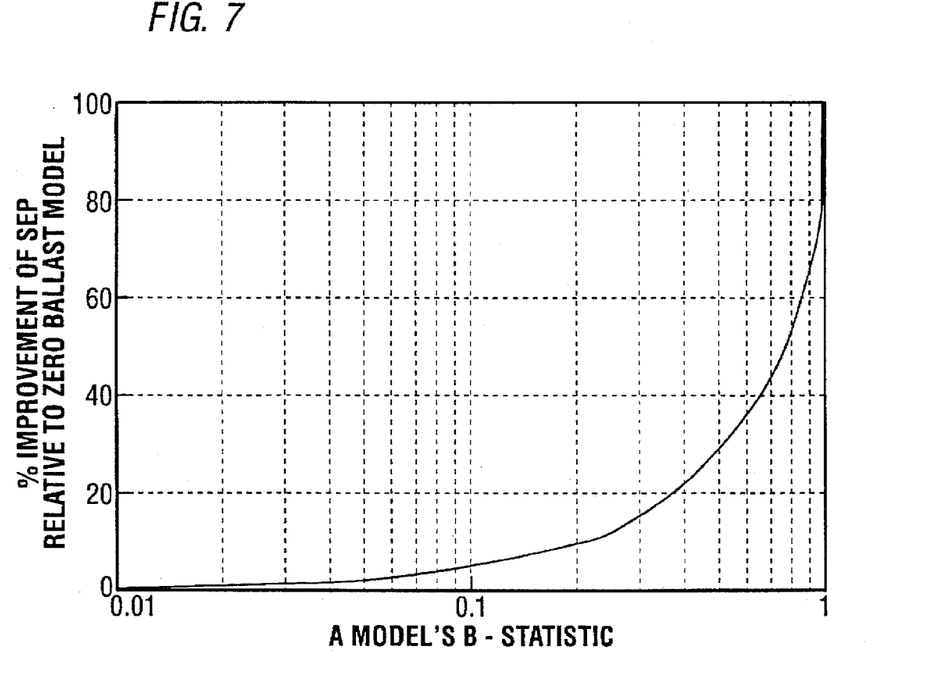
FIG. 7 illustrates the percentage improvement in the Standard Error of Prediction versus the B-statistic, which is $(1-R^2)$.

A "high-ballast" model is one which has a ballast of 0.2 to 0.4 corresponding to an $R^2$ of 0.8 to 0.6 between the different models' residuals. This can result in as much as a 25% improvement in the standard error of prediction over the original models. A ballast of 1.0 is a theoretical limit that cannot be reached. FIG. 7 plots a computer simulation of the upper bound for possible improvement in the Standard Error of Prediction versus the B-statistic, $(1-R^2)$, when the number of models being averaged and the number of samples whose residuals are being correlated are both very large.

Conceptually, this averaging has the effect of reducing "modeling noise" associated with some particular choice of samples in the calibration set, choice of wavelength regions, or types of preprocessing or postprocessing used in model development. This averaging also reduces the errors caused by unforeseen interferents that affect one region of the spectrum (which is used by some models) but that do not affect other regions of the spectrum (which are used by other models in the average). Of course, it will not compensate for samples whose lab values have systematic errors.

One benefit of selecting models to average based on their having poorly correlated residuals is that one can produce an average model which outperforms the best single model (as shown in an example below). However, another benefit is that one can save time and effort over brute force selection of which models to average based on direct calculation of the RMS residuals of averages of all possible pairs, triplets, etc. of model combinations. The amount of computation required by brute force selection increases linearly with the number of samples and increases factorially with the number of models.

To determine whether an average model is applicable to an unknown, one can compare the consistency with which many different models for the same property estimate approximately the same value for that property of the unknown. This is particularly useful for flagging inliers, for which no other reliable test exists. Inliers are unknowns in a spectral region which is too sparsely populated by known samples to insure good interpolation given the degree of local curvature of the response surface.

To determine whether an unknown sample is an inlier with respect to the average model, one first determines that it is not an outlier by using a standard Mahalanobis distance test. If it is not an outlier, then one uses each model in the average model to obtain an NIR-estimate of the property of interest for the unknown sample. An unknown is probably an inlier if the NIR estimates of these different models vary substantially, meaning their standard deviation is much larger than the average standard error of calibration of the models.

Specifically, the probability of an unknown being an inlier can be estimated from the square of the ratio of the standard deviation, $\sigma$, of different NIR models' estimates of the unknown to the average standard error of calibration (SEC) of these models. The inlier or I-statistic is defined as:

$$\text{I-statistic} = \sigma^2_{MME}/\sigma^2_{SEC} \qquad (6)$$

where, $\sigma^2_{MME}$=Variance of Many NIR Models' Estimates of the Same Sample $\sigma^2_{SEC}$=Square of Average Fit (SEC) of Models to Their Respective Calibration Sets≈Variance of Models' Fit to Their Respective Calibration Sets By defining the I-statistic as a ratio of variances (squares of standard deviations), one can make use of the standard F-distribution test for the probability that these two variances are equal. That is, the I-statistic can be compared to an F-distribution where the number of degrees of freedom for the numerator is the number of models whose estimates are being averaged and the number of degrees of freedom for the denominator is the average number of samples being fit by each model.

In the denominator of the definition of I-statistic, the SEC of any one of the models (instead of their average) could have been used because these models were selected based on their having SEC's that lie in a narrow range close to the lab-value uncertainty. That is, the numerical value of the average of the SEC of these models is approximately the same as the numerical value of the SEC of any particular model. However, to maintain symmetry in the definition, the I-statistic was simply defined as the average SEC of the models.

Conceptually, two distributions are being compared. The first is the distribution of the differences between the average estimate and M individual estimates (by M different NIR models) of the same sample. The second is the distribution of the differences between the directly-measured lab values and N estimates (by a single NIR model) of N different samples. It is assumed that each distribution is bell-shaped (normal), and each distribution's variance (the square of its standard deviation) is computed.

FIG. 6 is an I-statistic plot representing the case where 650 samples were fit by each model and 5 models were averaged. Here, the first distribution corresponds to 5 estimates of the same sample by 5 different NIR models and the second distribution corresponds to 650 estimates of 650 different samples by a single NIR model.

FIG. 6 illustrates whether the probability that the variance about the mean of 5 different NIR models' estimates of the same sample is greater than the variance of a single NIR model's estimation errors for 650 different samples. FIG. 6 illustrates the probability that the sample is an inlier, after it has already been tested and shown not to be an outlier. When the I-statistic is greater than about 1, the unknown is more likely an inlier than not.

Alternatively, one may calculate an inlier probability from the variance of estimates of NIR models whose calibration sets' samples were not chosen randomly but were chosen based on their chemical composition. Consider, for example, gasolines containing methyl tert-butyl ether (MTBE). One may perform inlier detection by looking at the variance of the estimates of different NIR models some of which are based only on MTBE-containing gasolines and some of which are based only on non-MTBE containing gasolines.

This approach is useful because certain mixtures of non-MTBE gasoline components appear almost the same spectrally as does MTBE in gasoline. This makes the response surface (particularly for physical properties) highly convoluted. Inlier detection is made easier by choosing a set of inlier-detection models which are based on the presence or absence of any chemical responsible for substantially increasing the convolution of the response surface. This makes it easier to flag as inliers those unknowns that lie in regions of spectral space where interpolation of the response surface is ambiguous. In such regions of spectral space, one needs more calibration samples to accurately map the highly-convoluted response surface.

In the hypothetical example discussed earlier, one started with 100 spectra, developed 30 models, selected the best-fitting 10 of the 30 and then averaged the least correlated 5 of these 10. U.S. Pat. No. 5,397,899 issued to DiFoggio et al, discusses averaging multiple models, but it does not discuss selecting which models to average based on the degree to which their residuals are correlated with one another.

We have tried averaging as many as 2,000 to 3,000 best-fitting models. However, we found that the results of averaging several thousand models were comparable to simply averaging the least-correlated 5 to 25 models of these 2,000 to 3,000 models. The least-correlated models contain the most independent information.

Figure 8A:
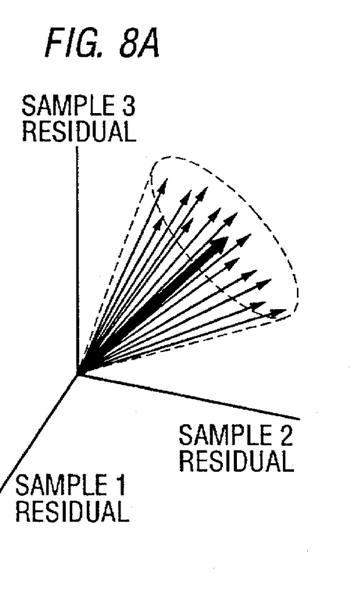
FIG. 8a schematically illustrates the residual vectors of several thousand models spread out roughly in a cone shape about their average residual vector.

Conceptually, one can understand this by plotting the residual vectors of many models for three calibration set samples as shown in FIG. 8a. Invariably, the residuals of different models that have good SEC's, are positively correlated to one another. Schematically, this is illustrated in FIG. 8a where the residual vectors of several thousand such models are spread out roughly in a cone about their average residual vector. Notice that the length of the average residual vector is 20–30% less than that of residual vectors on the periphery of the cone.

Figure 8B:
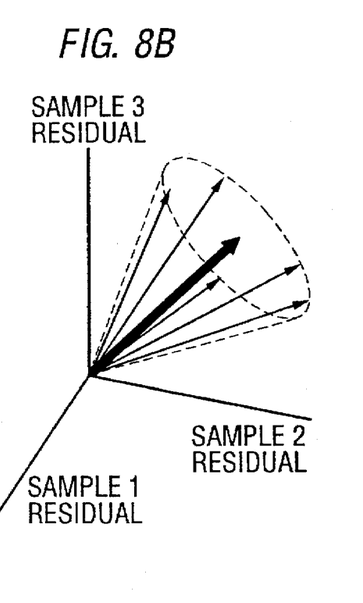
FIG. 8b schematically illustrates the residual vectors of five models whose residuals are the least positively correlated to one another.

By averaging only those models whose residuals are the least positively correlated to one another, such as those on the periphery of the cone, one need only average a few models to get approximately the same average residual vector as one would get by averaging several thousand models. The average of the five least correlated models is illustrated in FIG. 8b. This reasoning can be readily extended to more samples (more than 3 dimensions), but it would be difficult to illustrate this with a 2-dimensional drawing, such as provided in FIGS. 8a and 8b.

Consider a small data set of 11 validation samples and 5 models as a simple example to illustrate the concept of model ballast achieved through averaging the best models whose residuals are least correlated to one another. The 11 samples, which were not used in the calibration set, were exchange-group gasolines. They had been rated on many different engines in many different labs. The average octane numbers of such samples are more accurate than the octane numbers of singly-rated samples. Alternatively, one could have correlated the residuals of calibration samples instead of validation samples.

Table 2 lists 5 models' Motor Octane Number (MON) residuals for each of the 11 exchange-group validation gasolines along with each model's worst low residual, worst high residual, worst low minus worst high residual, and root-mean-square (RMS) residual. Table 3 lists the correlations, R, between the validation residuals of these 5 models.

The first step is to retain only the best models (#1, #4, #5) which have RMS residuals less than 0.35. From Table 3 one sees that the least correlated models in this set of best models are Models #1 and #4 (R=0.6252, B-statistic=1.0−$0.6252^2$= 0.6091).

It is important to choose an RMS residual cutoff for the "best" models as low as possible while still retaining a large enough pool of models from which to select those to be averaged. This is because one can get poor correlation between the residuals of two models simply because one model is much poorer (has a much worse RMS residual) than the other. However, averaging a poor model with a good model is unlikely to improve the RMS residual beyond that of the good model. The biggest improvement comes when equally good models (ones with nearly the same low RMS residual) have poorly correlated residuals and are averaged.

The residuals and other statistics for the model formed by averaging Model 1 and Model 4 are listed in Table 2. Notice that the RMS residual for this average model is 0.248 which is 10% better than the best RMS residual of any single model (Model #5 whose RMS=0.276) and 22% better than the average RMS error (0.319) of the two models (#1 and #4) from which the average model is composed. These numbers are consistent with the simulation of FIG. 7 where 38% is shown as the upper bound for improvement in RMS residual for a ballast of 0.6091. Also notice that the worst high minus worst low residual is now 0.72 which is 17% better than for any single model.

Tables 4–6 show an example of inlier detection. These tables compare five different NIR model's estimations of Research, Motor, and Pump Octane Number, respectively, for the same 20 unknown samples. Each table also lists the average of the 5 estimations, and the standard deviation, $\sigma$, about the average.

Here, samples are flagged as outliers whenever their Mahalanobis distance ratio, MDR, exceeds 1.0. Here, the Mahalanobis distance ratio is defined as the square of the sample's Mahalanobis distance divided by twice the square of the root-mean-square Mahalanobis distance, so MDR= $(D^2/2D^2_{RMS})$ and, it too, is listed in each table.

Only samples that are not outliers are considered for inlier status. The I-statistic is calculated as $(\sigma/SEC)^2$ where the SECs that are used here are 0.26 for RON, 0.23 for MON, and 0.21 for PON. For 5 models and 650 samples in each model, the corresponding F-distribution probability becomes 95% at 2.26, as illustrated in FIG. 6.

Here, samples (that are not outliers) are flagged as inliers whenever there is more than a 95% probability that they are an inlier. That is, whenever the I-statistic/2.26 exceeds 1.0 as shown in each table.

Figure 9:
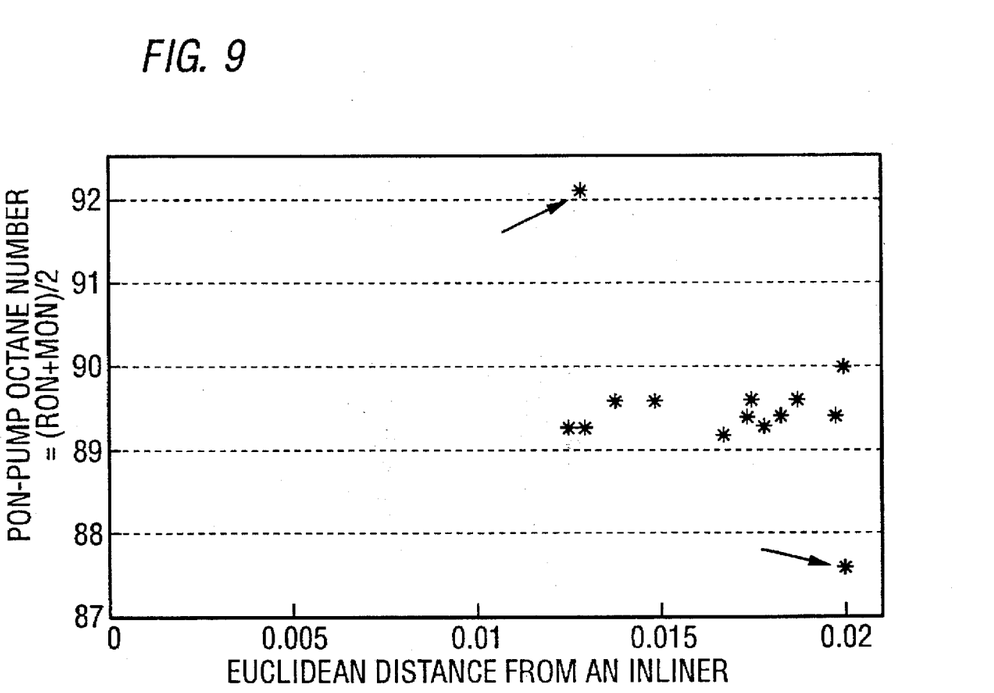
FIG. 9 shows the variation in Pump Octane Number for 15 samples in a calibration set that were nearest (in Euclidean distance) to an inlier sample.

Even in Euclidean absorbance space, the rapid change in octane number within a small radius of an inlier is apparent. FIG. 9 shows the variation in Pump Octane Number for those 15 samples in our calibration set that were nearest (in Euclidean distance) to an inlier sample (Sample 1 in Tables 4–6).

In FIG. 9, the inlier sample is at the abscissa origin. Note that the octane numbers of the nearest calibration set samples vary by approximately 6 octane numbers which is why model interpolation at this inlier's position in spectral space is risky. To lower the risk of interpolation error, one needs additional calibration samples that are in closer spectral proximity to the inlier.

The foregoing description is directed to particular embodiments of the present invention for the purpose of illustration and explanation. It will be apparent, however, to one skilled in the art that many modifications and changes to the embodiment set forth above are possible without departing from the scope and the spirit of the invention. It is intended that the following claims be interpreted to embrace all such modifications and changes.

TABLE 1

Hypothetical Function in Equation 3
Calculated for Selected Values of x

| x | F(x) |
|---|------|
| 0.00 | –.000001 |
| 0.04 | .039997 |
| 0.08 | .079990 |
| 0.12 | .119962 |
| 0.16 | .159868 |
| 0.20 | .199576 |
| 0.24 | .238734 |
| 0.28 | .276482 |
| Gap in data where inliers can occur. | |
| 0.93 | .836732 |
| 0.96 | .941438 |
| 1.00 | 1.000045 |
| 1.04 | 1.058658 |
| 1.07 | 1.163373 |
| Gap in data where inliers can occur. | |
| 1.70 | 1.709974 |
| 1.74 | 1.746804 |

TABLE 1-continued

Hypothetical Function in Equation 3
Calculated for Selected Values of x

| x | F(x) |
|---|------|
| 1.78 | 1.785567 |
| 1.82 | 1.824835 |
| 1.86 | 1.863949 |
| 1.90 | 1.902709 |
| 1.94 | 1.941281 |
| 1.98 | 1.980181 |
| 2.02 | 2.020220 |
| 2.06 | 2.062324 |
| 2.10 | 2.107311 |
| 2.14 | 2.155723 |

End of data beyond which outliers can occur.

TABLE 2

Residual Table for 5 Models and 1 Average Model for Motor Octane Number Used to Predict 11 Exchange Group Samples of Gasolines

|  | Model 1 | Model 2 | Model 3 | Model 4 | Model 5 | Avg 1 & 4 |
|---|---|---|---|---|---|---|
| Sample 1 | .50 | .85 | .74 | –.02 | .04 | .240 |
| Sample 2 | –.45 | –.29 | –.19 | –.27 | –.21 | –.360 |
| Sample 3 | .02 | –.36 | –.23 | –.49 | –.26 | –.235 |
| Sample 4 | .18 | .21 | .54 | –.11 | .03 | .035 |
| Sample 5 | .32 | .42 | .27 | –.06 | .28 | .130 |
| Sample 6 | .28 | .92 | .57 | –.02 | .28 | .130 |
| Sample 7 | .54 | .52 | .52 | .18 | .49 | .360 |
| Sample 8 | .28 | .50 | .55 | .29 | .31 | .285 |
| Sample 9 | .40 | .47 | .52 | .03 | .17 | –.215 |
| Sample 10 | .01 | .28 | –.31 | –.68 | –.38 | –.335 |
| Sample 11 | .38 | .75 | .16 | –.04 | .24 | .179 |
| Worst Low Res | –.45 | –.36 | –.31 | –.68 | –.38 | –.360 |
| Worst Hi Res | .54 | .92 | .74 | .29 | .49 | .360 |
| Worst Hi-Low | .99 | 1.28 | 1.05 | .97 | .87 | .720 |
| RMS residual | .349 | .555 | .456 | .288 | .276 | .248 |

TABLE 3

Correlation Table for Residuals of 5 Models for Motor Octane Number Used to Predict 11 Exchange Group Samples of Gasoline

| R | Model 1 | Model 2 | Model 3 | Model 4 | Model 5 |
|---|---|---|---|---|---|
| Model 1 | 1.0000 | .7870 | .7547 | .6252 | .7383 |
| Model 2 | .7870 | 1.0000 | .7229 | .5722 | .6584 |
| Model 3 | .7547 | .7229 | 1.0000 | .8378 | .7514 |
| Model 4 | .6252 | .5722 | .8378 | 1.0000 | .9102 |
| Model 5 | .7383 | .6584 | .7514 | .9102 | 1.0000 |

TABLE 4

Inlier Detection Example for Research Octane Number

| Sample Number | RON Mod 1 | RON Mod 2 | RON Mod 3 | RON Mod 4 | RON Mod 5 | RON Avg | RON σ | I-stat / 2.26 | RON MDR | MDR >1 Outlier | 95% Prob Inlier |
|---|---|---|---|---|---|---|---|---|---|---|---|
| 1 | 96.37 | 94.06 | 94.33 | 94.43 | 96.67 | 95.172 | 1.2425 | 15.49 | 0.693 | No | Yes |
| 2 | 93.87 | 93.57 | 93.62 | 93.64 | 93.98 | 93.736 | .1787 | .32 | 0.386 | No | No |
| 3 | 98.57 | 93.97 | 94.07 | 94.25 | 98.70 | 95.912 | 2.4882 | 62.12 | 0.794 | No | Yes |
| 4 | 99.49 | 91.60 | 91.96 | 92.27 | 99.81 | 95.026 | 4.2293 | 179.47 | 1.19 | Yes | — |
| 5 | 92.83 | 92.48 | 92.75 | 92.76 | 92.76 | 92.716 | .1358 | .19 | 0.387 | No | No |
| 6 | 96.08 | 95.98 | 96.27 | 96.28 | 96.29 | 96.180 | .1416 | .20 | 0.425 | No | No |
| 7 | 112.50 | 113.90 | 116.90 | 117.00 | 111.20 | 114.300 | 2.6010 | 67.88 | 1.4 | Yes | — |
| 8 | 95.80 | 93.75 | 94.08 | 94.14 | 95.88 | 94.730 | 1.0245 | 10.53 | 1.48 | Yes | — |
| 9 | 93.77 | 93.27 | 93.31 | 93.33 | 93.95 | 93.526 | .3122 | .98 | 0.483 | No | No |
| 10 | 95.00 | 94.21 | 94.13 | 94.11 | 95.23 | 94.536 | .5361 | 2.88 | 1.03 | Yes | — |
| 11 | 94.98 | 94.07 | 93.99 | 93.98 | 95.32 | 94.468 | .6350 | 4.05 | 1.01 | Yes | — |
| 12 | 92.80 | 92.71 | 92.99 | 92.95 | 93.34 | 92.958 | .2416 | .59 | 1.09 | Yes | — |
| 13 | 94.70 | 94.81 | 94.82 | 94.80 | 95.01 | 94.828 | .1126 | .13 | 1.07 | Yes | — |
| 14 | 92.58 | 92.37 | 92.27 | 92.25 | 92.46 | 92.386 | .1372 | .19 | 0.681 | No | No |
| 15 | 96.22 | 95.21 | 95.27 | 95.28 | 96.18 | 95.632 | .5194 | 2.71 | 0.928 | No | Yes |
| 16 | 100.4 | 93.26 | 93.45 | 93.74 | 100.60 | 96.290 | 3.8476 | 148.54 | 0.881 | No | Yes |
| 17 | 95.04 | 94.45 | 94.36 | 94.39 | 95.75 | 94.798 | .6009 | 3.62 | 0.550 | No | Yes |
| 18 | 94.28 | 94.62 | 94.35 | 94.28 | 94.53 | 94.412 | .1548 | .24 | 1.54 | Yes | — |
| 19 | 92.45 | 92.08 | 92.22 | 92.25 | 92.75 | 92.350 | .2597 | .68 | 0.396 | No | No |
| 20 | 98.54 | 93.45 | 93.70 | 93.89 | 98.34 | 95.584 | 2.6128 | 68.50 | 0.420 | No | Yes |

TABLE 5

Inlier Detection Example for Motor Octane Number

| Sample Number | MON Mod 1 | MON Mod 2 | MON Mod 3 | MON Mod 4 | MON Mod 5 | MON Avg | MON σ | I-stat / 2.26 | MON MDR | MDR >1 Outlier | 95% Prob Inlier |
|---|---|---|---|---|---|---|---|---|---|---|---|
| 1 | 85.24 | 82.95 | 83.57 | 83.52 | 85.67 | 84.190 | 1.1899 | 9.27 | 0.479 | No | Yes |
| 2 | 83.37 | 82.91 | 83.29 | 83.29 | 83.49 | 83.270 | .2173 | .31 | 0.522 | No | No |
| 3 | 87.90 | 82.96 | 83.55 | 83.39 | 88.11 | 85.182 | 2.5871 | 43.81 | 0.887 | No | Yes |
| 4 | 87.85 | 79.32 | 79.85 | 79.61 | 88.31 | 82.988 | 4.6550 | 141.84 | 1.33 | Yes | — |
| 5 | 83.23 | 82.77 | 83.37 | 83.37 | 83.28 | 83.204 | .2500 | .41 | 0.639 | No | No |
| 6 | 85.24 | 84.92 | 85.57 | 85.56 | 85.45 | 85.348 | .2736 | .49 | 0.561 | No | No |
| 7 | 95.66 | 97.12 | 95.67 | 96.01 | 94.71 | 95.834 | .8668 | 4.92 | 22.9 | Yes | — |
| 8 | 85.20 | 83.64 | 84.69 | 84.65 | 85.71 | 84.778 | .7691 | 3.87 | 2.17 | Yes | — |
| 9 | 82.96 | 82.52 | 83.07 | 83.09 | 83.33 | 82.994 | .2974 | .58 | 0.380 | No | No |
| 10 | 85.17 | 85.36 | 85.68 | 85.69 | 85.45 | 85.470 | .2208 | .32 | 1.33 | Yes | — |
| 11 | 85.17 | 85.33 | 85.64 | 85.64 | 85.51 | 85.458 | .2051 | .28 | 1.27 | Yes | — |
| 12 | 82.78 | 83.11 | 83.56 | 83.54 | 83.45 | 83.288 | .3367 | .74 | 0.857 | No | No |
| 13 | 84.96 | 85.24 | 85.49 | 85.48 | 85.04 | 85.242 | .2442 | .39 | 1.06 | Yes | — |
| 14 | 82.89 | 83.19 | 83.38 | 83.35 | 82.93 | 83.148 | .2294 | .34 | 0.646 | No | No |
| 15 | 85.29 | 85.05 | 85.36 | 85.36 | 85.40 | 85.292 | .1410 | .13 | 1.22 | Yes | — |
| 16 | 87.95 | 80.18 | 81.37 | 81.18 | 88.13 | 83.762 | 3.9319 | 101.19 | 1.01 | Yes | — |
| 17 | 84.55 | 83.90 | 84.72 | 84.72 | 84.93 | 84.564 | .3949 | 1.02 | 0.713 | No | Yes |
| 18 | 82.68 | 83.27 | 83.59 | 83.61 | 82.99 | 83.228 | .3986 | 1.04 | 1.47 | Yes | — |
| 19 | 82.58 | 81.90 | 82.66 | 82.67 | 82.68 | 82.498 | .3366 | .74 | 0.562 | No | No |
| 20 | 88.11 | 83.20 | 84.09 | 83.97 | 88.28 | 85.530 | 2.4574 | 39.53 | 0.660 | No | Yes |

TABLE 6

Inlier Detection Example for Pump Octane Number = (RON + MON)/2

| Sample Number | PON Mod 1 | PON Mod 2 | PON Mod 3 | PON Mod 4 | PON Mod 5 | PON Avg | PON σ | I-stat / 2.26 | PON MDR | MDR >1 Outlier | 95% Prob Inlier |
|---|---|---|---|---|---|---|---|---|---|---|---|
| 1 | 90.91 | 88.52 | 89.10 | 88.57 | 90.80 | 89.580 | 1.1865 | 11.78 | 0.692 | No | Yes |
| 2 | 88.72 | 88.29 | 88.53 | 88.31 | 88.45 | 88.460 | .1761 | .26 | 0.386 | No | No |
| 3 | 93.41 | 88.49 | 89.07 | 87.77 | 93.12 | 90.372 | 2.6827 | 60.20 | 0.819 | No | Yes |
| 4 | 93.44 | 85.44 | 86.32 | 84.18 | 93.97 | 88.670 | 4.6626 | 181.84 | 1.30 | Yes | — |
| 5 | 88.13 | 87.66 | 88.16 | 88.00 | 87.78 | 87.946 | .2190 | .40 | 0.387 | No | No |

TABLE 6-continued

Inlier Detection Example for Pump Octane Number = (RON + MON)/2

| Sample Number | PON Mod 1 | PON Mod 2 | PON Mod 3 | PON Mod 4 | PON Mod 5 | PON Avg | PON σ | I-stat / 2.26 | PON MDR | MDR >1 Outlier | 95% Prob Inlier |
|---|---|---|---|---|---|---|---|---|---|---|---|
| 6 | 90.78 | 90.48 | 90.94 | 90.83 | 90.64 | 90.734 | .1783 | .27 | 0.432 | No | No |
| 7 | 103.1 | 105.4 | 106.8 | 106.3 | 102.10 | 104.740 | 2.0477 | 35.07 | 30.4 | Yes | — |
| 8 | 90.79 | 88.70 | 89.34 | 89.16 | 90.41 | 89.680 | .8820 | 6.51 | 1.49 | Yes | — |
| 9 | 88.40 | 87.94 | 88.24 | 88.24 | 88.37 | 88.238 | .1820 | .28 | 0.503 | No | No |
| 10 | 90.30 | 89.80 | 90.01 | 90.06 | 89.89 | 90.012 | .1904 | .30 | 1.03 | Yes | — |
| 11 | 90.28 | 89.70 | 89.94 | 89.97 | 89.97 | 89.972 | .2061 | .36 | 1.01 | Yes | — |
| 12 | 87.87 | 87.90 | 88.36 | 88.38 | 87.97 | 88.096 | .2528 | .53 | 1.09 | Yes | — |
| 13 | 89.89 | 90.12 | 90.23 | 90.27 | 89.70 | 90.042 | .2416 | .49 | 1.06 | Yes | — |
| 14 | 87.95 | 87.80 | 87.93 | 87.86 | 87.18 | 87.744 | .3208 | .86 | 0.682 | No | No |
| 15 | 90.91 | 90.11 | 90.38 | 90.27 | 90.38 | 90.410 | .3006 | .76 | 0.930 | No | No |
| 16 | 94.33 | 86.74 | 87.63 | 85.83 | 94.11 | 89.728 | 4.1504 | 144.08 | 0.927 | No | Yes |
| 17 | 89.99 | 89.23 | 89.53 | 89.67 | 90.09 | 89.702 | .3489 | 1.02 | 0.601 | No | Yes |
| 18 | 88.58 | 88.99 | 88.97 | 88.94 | 88.51 | 88.798 | .2330 | .45 | 1.54 | Yes | — |
| 19 | 87.65 | 87.04 | 87.40 | 87.49 | 87.58 | 87.432 | .2385 | .48 | 0.415 | No | No |
| 20 | 93.46 | 88.34 | 89.08 | 88.02 | 93.21 | 90.422 | 2.6883 | 60.45 | 0.432 | No | Yes |

What is claimed is:

1. A method for determining a property of interest of a test sample by utilizing a plurality of samples, each having a known value of the property of interest, comprising:
   (a) subjecting each sample in the plurality of samples to a known light energy and collecting a corresponding spectrum for each such sample;
   (b) grouping the samples in the plurality of samples into a plurality of subsets;
   (c) determining a model for each such subset from the corresponding spectra of the samples in such subset;
   (d) selecting a group of models from the models determined for the each of the subsets based on a predetermined criterion;
   (e) retaining a subset of models from the group of models having residuals that are least correlated to one another; and
   (f) determining a composite model from the retained models to determine the property of interest of the test sample.

2. The method of claim 1 further comprising determining the applicability of the composite model to the test sample by utilizing a disparity in predictions of the retained models for the test sample.

3. The method of claim 1 further comprising:
   (i) determining a spectrum of the test sample; and
   (ii) determining the property of interest of the test sample by utilizing the composite model.

4. The method of claim 3, wherein the property of interest is an octane number.

5. The method of claim 3, wherein the property of interest is a cetane number.

6. The method of claim 3, wherein the property of interest is a chemical composition.

7. The method of claim 3, wherein each sample in the plurality of samples is a sample of gasoline.

8. The method of claim 3, wherein each sample in the plurality of samples is a sample of diesel fuel.

9. The method of claim 3, wherein each sample in the plurality of samples is a sample of refinery component stream.

10. The method of claim 3, wherein the samples are subjected to a near-infrared energy and the spectrum is a corresponding near-infrared spectrum.

11. The method of claim 10, wherein each model is a regression model.

12. The method of claim 1, wherein the predetermined criterion is a value of the standard errors of calibration.

13. The method of claim 1, wherein the property of interest is a physical property of the test sample.

14. The method of claim 1, wherein the property of interest is a chemical property of the test sample.

15. A method for developing a model for determining a property of interest of a test sample:
   (a) obtaining a plurality of samples of a material having known values of the property of interest;
   (b) collecting a near-infrared spectrum of each of the samples in the plurality of samples;
   (c) grouping the samples in the plurality of samples into a plurality of subsets;
   (d) determining a regression model for each subset from the near-infrared spectra of the samples forming such subset;
   (e) selecting regression models which have a standard error of calibration less than a predetermined value;
   (f) retaining regression models from the selected models which are relatively poorly correlated to each other;
   (g) averaging the retained models to determine a composite model;
   (h) determining a near-infrared spectrum of the test sample; and
   (i) determining the property of interest of the test sample by applying the composite model to the near-infrared spectrum of the test sample.

16. A method of determining the value of a property of interest of a test material, comprising:
   (a) obtaining a plurality of samples of the material, each such sample having a known value of the property of interest;
   (b) collecting a near-infrared spectrum for each sample in the plurality of samples using near-infrared radiation;
   (c) determining a separate regression model for a plurality of subsets of the plurality of samples;
   (d) selecting regression models having a standard error of calibration less than a predetermined value;
   (e) determining a residual for each sample and each selected regression model as the difference between a value of the property of interest determined by such selected regression model and a value determined by a primary measurement technique for the parameter of interest;

(f) pairing the regression models having any common samples;

(g) determining a correlation coefficient between residuals of common samples in each of the pairs of models;

(h) selecting a subset of selected regression models, wherein the residuals of the regression models in the subset are the least correlated to one another;

(i) averaging the models in the selected subset (Step h) to obtain a composite model;

(j) estimating the degree of improvement of the composite model estimates using a B-statistic, wherein the B-statistic is defined as $1-R^2$, where R is the average correlation coefficient between residuals of the subset of the least-correlated models;

(k) collecting a near-infrared spectrum of the test sample; and (l) computing the value of the parameter of interest of the test sample using the composite model.

17. The method of claim 16 further comprising comparing the computed value of the parameter of interest as calculated by each model in the subset of least-correlated models to determine the likelihood of interpolation error.

18. The method of claim 16, further comprising:

(i) determining whether the property of interest of the test sample is an outlier; and (ii) Determining an I-statistic for the computed value of the parameter of interest of the test sample using the subset of least correlated models, wherein the I-statistic is defined as a ratio of the variance of the subset models' estimates of the parameter of interest to the square of the average standard error of calibration of the subset models.

19. The method of claim 18, wherein an I-statistic greater than about 1 indicates that the computed value of the parameter of interest of the test sample is more likely an inlier than not.

20. The method of claim 19, wherein the test sample material is gasoline and the property of interest is an octane number of the gasoline.

21. A method for determining a property of interest of a test sample by utilizing a plurality of samples, each having a known value of the property, comprising:

(a) subjecting each sample in the plurality of samples to a known light energy and collecting a corresponding spectrum for each such sample;

(b) determining a composite model from the spectra of the plurality of samples;

(c) determining a spectrum of the test sample;

(d) determining the property of interest of the test sample by applying the composite model to the spectrum of the test sample;

(e) determining whether the property of interest of the test sample is an outlier; and (f) determining an I-statistic for the parameter of interest of the test sample if the test sample is not an outlier, wherein the I-statistic is defined as a ratio of the variance of the subset models' estimates of the parameter of interest to the square of the average standard error of calibration of the subset models.

(g) predicting the test sample to be an inlier if the value of the I-statistic of the parameter of interest of the test sample is greater than about 1.

22. The method of claim 21, wherein the samples are subjected to near-infrared light energy and the spectra are near-infrared spectra.

23. The method of claim 21, wherein each model is a regression model.

* * * * *